United States Patent [19]
Bogue et al.

[11] Patent Number: 5,653,926
[45] Date of Patent: Aug. 5, 1997

[54] METHOD AND APPARATUS FOR FORMING COMPRESSION DOSAGE UNITS

[75] Inventors: Beuford Arlie Bogue, Broad Run; Garry L. Myers, Reston, both of Va.

[73] Assignee: Fuisz Technologies, Ltd., Chantilly, Va.

[21] Appl. No.: 437,300

[22] Filed: May 9, 1995

Related U.S. Application Data

[63] Continuation-in-part of Ser. No. 276,244, Jul. 18, 1994, Pat. No. 5,616,344, which is a continuation-in-part of Ser. No. 259,496, Jun. 14, 1994, abandoned, and Ser. No. 259,258, Jun. 14, 1994, which is a continuation-in-part of Ser. No. 133,669, Oct. 7, 1993, Pat. No. 5,597,416, and Ser. No. 119,974, Sep. 10, 1993, Pat. No. 5,518,551.

[51] Int. Cl.$^6$ .................................. B29C 43/04
[52] U.S. Cl. ..................... 264/120; 264/109; 264/123; 425/345; 425/348 R; 425/352; 425/353
[58] Field of Search ........................ 264/109, 120, 264/123; 425/344, 345, 347, 348 R, 350, 352, 353

[56] References Cited

U.S. PATENT DOCUMENTS

| | | | |
|---|---|---|---|
| 2,068,619 | 1/1937 | Bailey | 107/17 |
| 2,214,505 | 9/1940 | Magnenat | 18/16 |
| 2,970,554 | 2/1961 | Haupt | 425/347 |
| 3,999,922 | 12/1976 | Shimada | 425/353 |
| 4,106,160 | 8/1978 | Jentsch | 425/353 |
| 4,376,111 | 3/1983 | Tovey | 424/15 |
| 4,493,822 | 1/1985 | Tovey | 424/15 |
| 4,880,373 | 11/1989 | Balog et al. | 425/149 |
| 4,943,227 | 7/1990 | Facchini | 425/345 |
| 5,407,339 | 4/1995 | Fehlhafer | 425/345 |

*Primary Examiner*—Mary Lynn Theisen
*Attorney, Agent, or Firm*—Hoffmann & Baron

[57] ABSTRACT

A method and apparatus provides for the formation of compression dosage units from tableting feedstock. A feedstock dossiter is provided including an open ended chamber for insertion into a reservoir containing the tableting feedstock. The dossiter includes a movable die punch which is movable within the chamber between at least two positions. A first position away from the open end of the chamber provides for the collection of a preselected volume of tableting feedstock from the reservoir. The die punch is movable to a second position which effects formation of the tablet within the accumulation chamber. The dossiter shown herein may be used in combination with a fixed die punch to form the tablet.

26 Claims, 6 Drawing Sheets

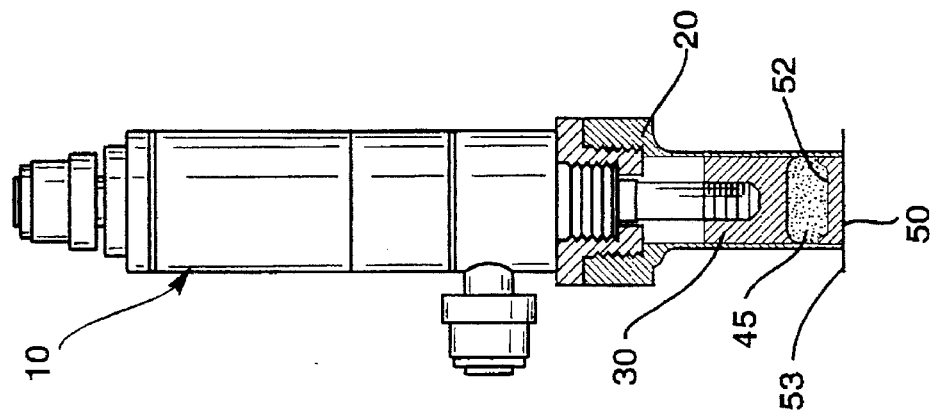
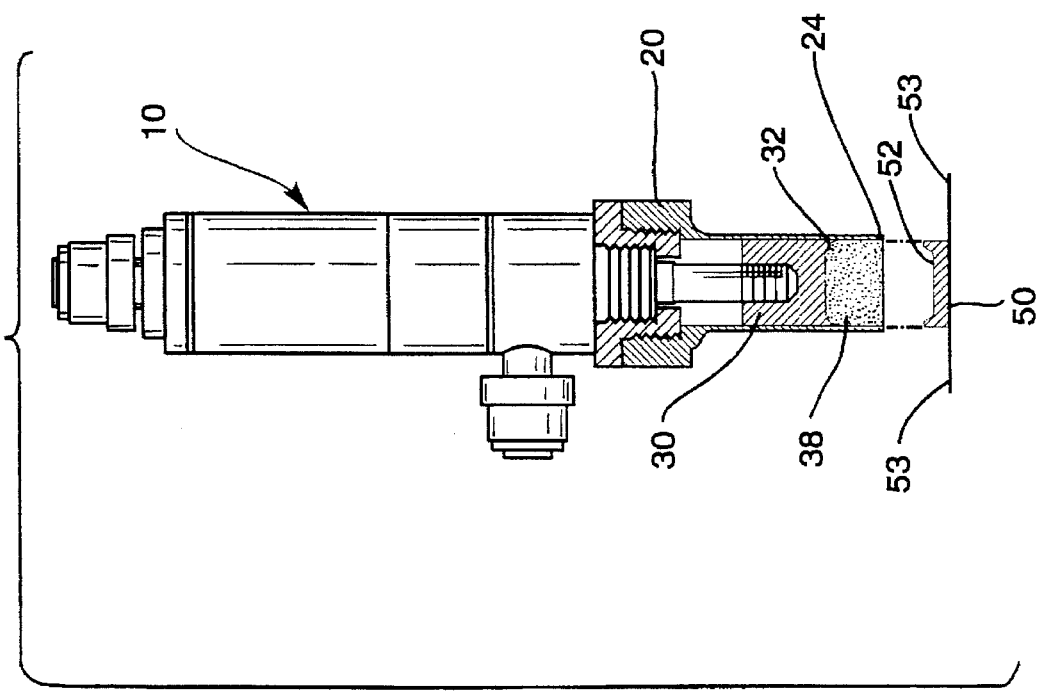

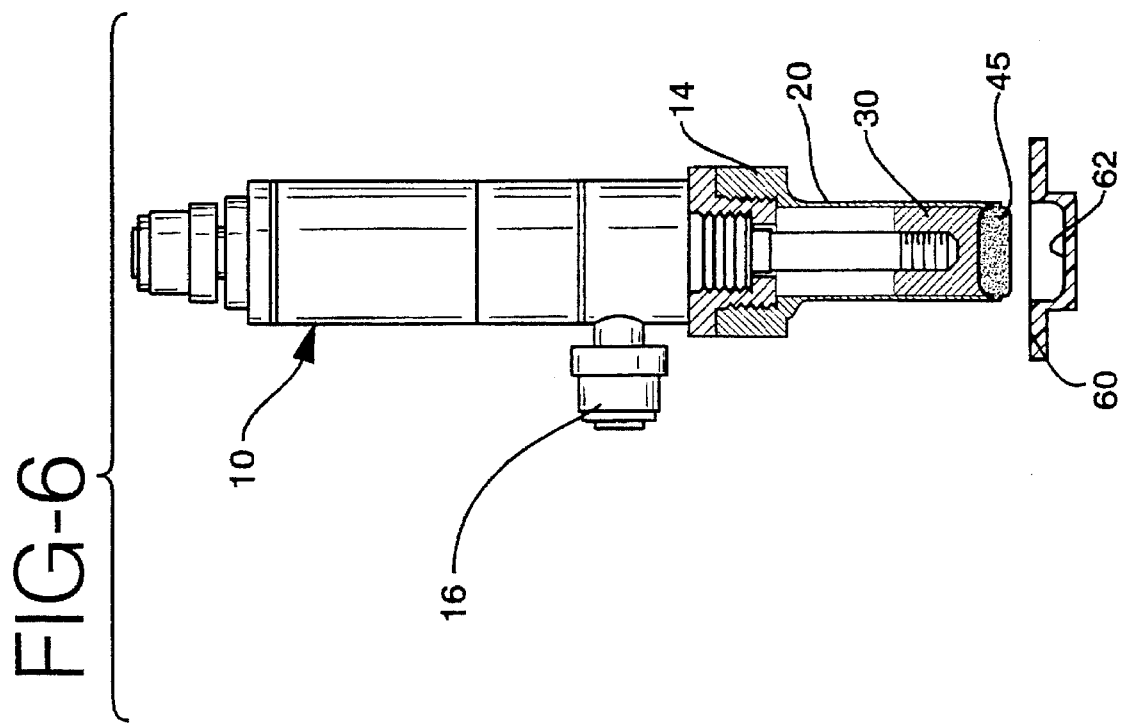

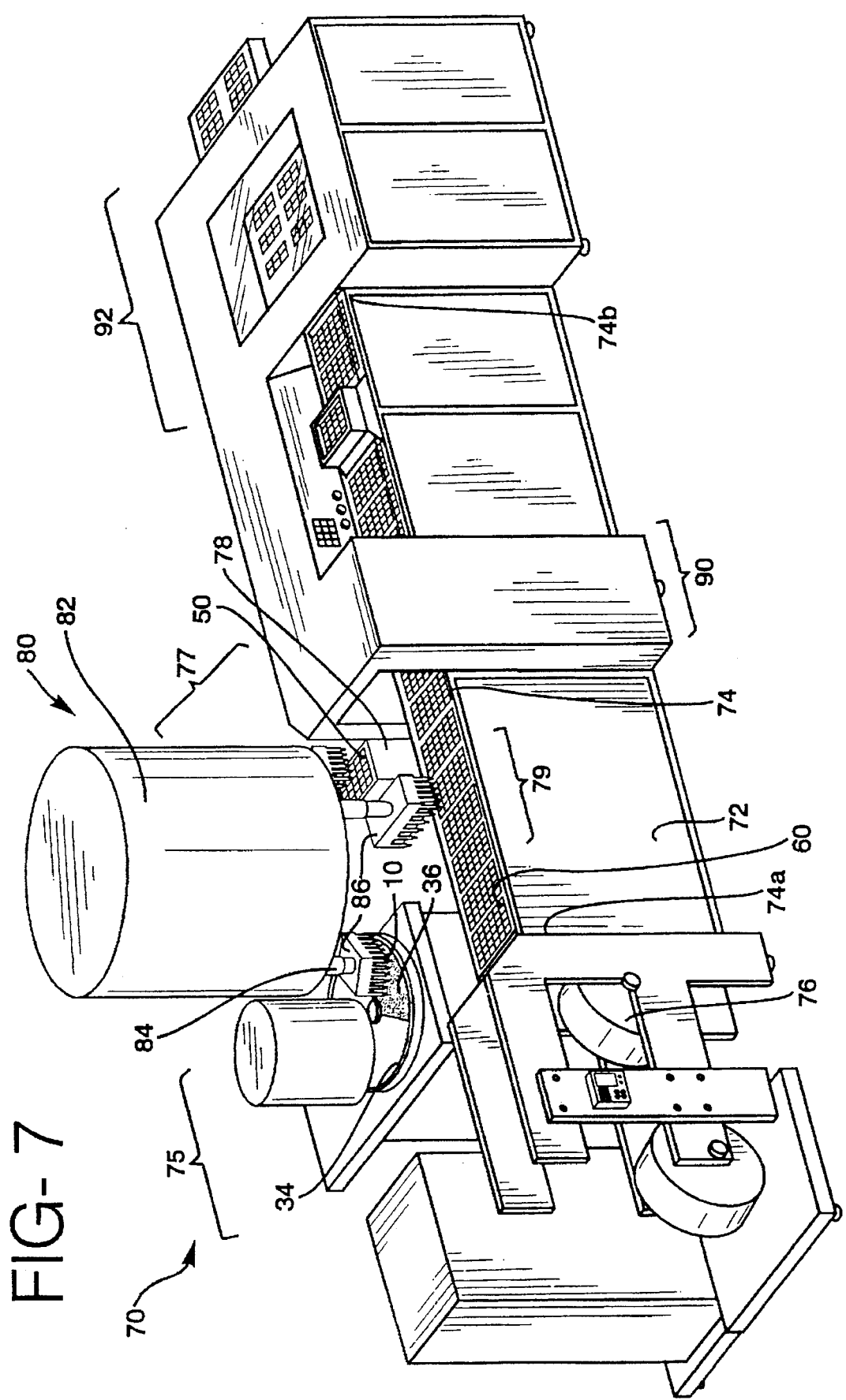

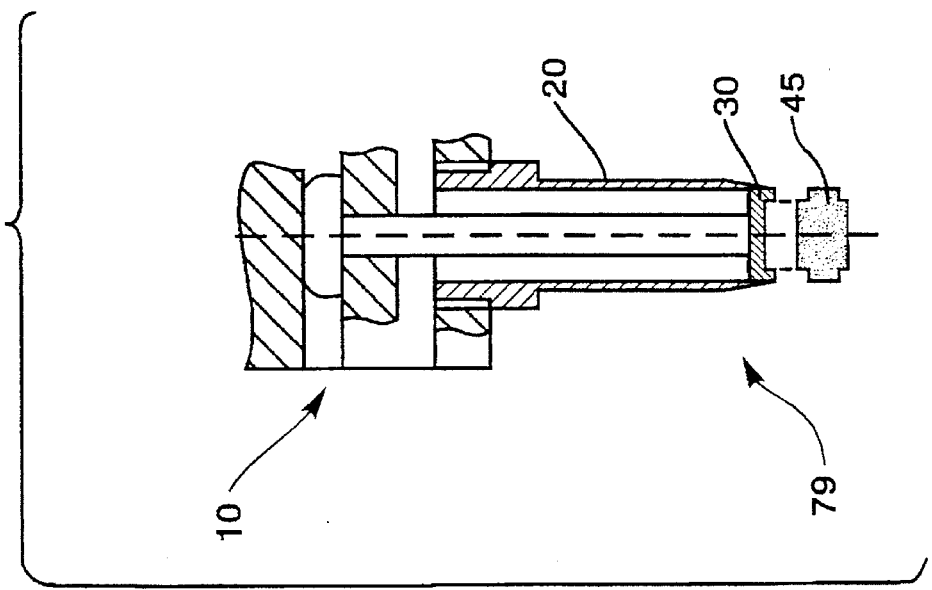
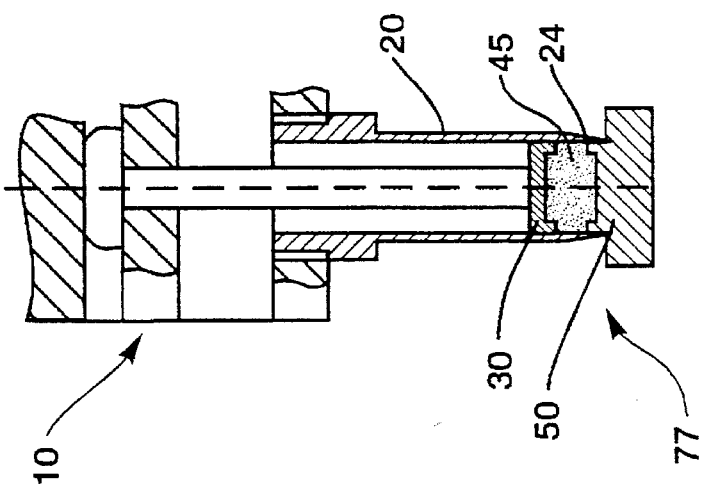
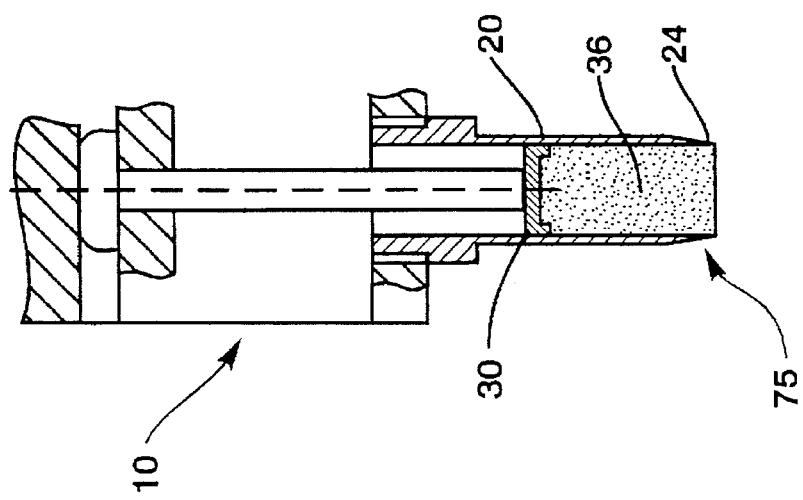

METHOD AND APPARATUS FOR FORMING COMPRESSION DOSAGE UNITS

CROSS REFERENCE TO RELATED APPLICATIONS

The present application is a continuation-in-part of U.S. application Ser. No. 08/276,244 filed Jul. 18, 1994 (Attorney's Docket No. 447-103) from U.S. Pat. No. 5,616, 344 which is a continuation-in-part of U.S. application Ser. No. 08/259,496 filed Jun. 14, 1994 (Attorney's Docket No. 447-105)now abandoned, and U.S. application Ser. No. 08/259,258 filed Jun. 14, 1994 (Attorney's Docket No. 447-106), which is a continuation-in-part of U.S. application Ser. No. 08/133,669 filed Oct. 7,1993 (Attorney's Docket No. 447-66) now U.S. Pat. No. 5,597,416 and U.S. application Ser. No. 08/119,974 filed Sep. 10, 1993 (Attorney's Docket No., 447-85) now U.S. Pat. No. 5,518,551. The contents of each of these commonly-owned applications is incorporated herein by reference.

FIELD OF THE INVENTION

The present invention relates generally to a method and apparatus for forming compression dosage units, more specifically tablets. The present invention more particularly relates to forming tablets, preferably low density tablets, within the dossiter used to collect the tableting feedstock.

BACKGROUND OF THE INVENTION

Dosage units in the form of tablets are prepared by compressing a formulation containing a medicinal substance or drug and other ingredients, such as excipients selected for properties which enhance the production and use of the tablet. There are currently three known basic methods for preparing tablet granulations. These are wet granulation, dry granulation and direct compression. Both wet and dry granulations involve the formation of an agglomerate for feeding to a die cavity. Direct compression usually involves compressing a powder blend of an active ingredient with suitable excipients.

Other methods of preparing feedstock for preparing compression dosage units have been disclosed in the above-referenced copending applications as well as in copending, commonly owned U.S. application Ser. No. 08/194,682 filed Feb. 10, 1994, mentioned above. Each of these applications are incorporated herein by reference.

U.S. application Ser. No. 08/194,682 discloses a method of making a solid comestible by compressing shearform matrix masses sufficiently to form a comestible compression unit. U.S. application Ser. No. 08/259,496 discloses a method of preparing a quick dissolve low density comestible unit by mixing uncured shearform matrix and an additive, molding a unit dosage form therefrom, and curing the shearform matrix. Finally, U.S. application Ser. No. 08/259, 258 discloses a method of preparing quick dissolve comestible units by initiating crystallization of shearform matrix, and combining, either before or after initiating crystallization, an additive with the shearform matrix to form flowable, compactible micro-particulates. Finally, the micro-particulate medium is compacted to form the quick dissolve comestible unit. In each of these disclosures, the tableting medium is prepared initially by use of shearform matrix. In most cases a quick dissolve tablet can be produced by providing a compressed body which is of low density and capable of being disintegrated and dispersed relatively rapidly, and in many cases, instantaneously.

Tableting processes known today in the art generally include the use of a machine which includes opposing punches and cavities into which a tableting medium can be directed and subjected to compression between the punches. See, for example, U.S. Pat. No. 4,943,227; U.S. Pat. No. 4,880,373; U.S. Pat. No. 2,214,505 and U.S. Pat. No. 2,068,619. Other references which disclose different shapes of dosage units are U.S. Pat. No. 4,493,822, U.S. Pat. No. 4,376,111, and an excerpt from The Consumer Guide for "Prescription Drugs," p. 194–208, Publications International, Ltd. (1990).

In the manufacture of low density tablets from tableting feedstock, the feedstock is provided in a reservoir or other container. A premeasured amount of tableting feedstock must be transferred from the reservoir to the apparatus which forms the tablet, typically an array of punches and dies. The tablet is formed between the punches within the dies and then must be transferred to a product package. Obviously there are numerous processing steps involved in moving from tableting feedstock to finished tablet.

Such excess handling has significant drawbacks. The processing time is increased as is the complexity of the apparatus used to form tablets. Additional handling of the finished tablet increases the chances of tablet breakage. Also, product consistency may suffer as a result of the numerous steps involved in forming a tablet.

It is therefore desirable to provide a method and apparatus of employing the dossiter in the formation of the tablets, preferably low density tablets. This will enable the tablet to be formed and packaged with minimal processing steps and equipment.

SUMMARY AND OBJECTS OF THE INVENTION

It is an object of the present invention to provide a method and apparatus for forming compression dosage units from tableting feedstock. The apparatus includes a feedstock dossiter having an open ended accumulation chamber for insertion into the tableting feedstock reservoir. A movable die punch is movably supported within the chamber between at least two positions. A first position effects collection of a predetermined volume of tableting feedstock from the reservoir. An optional second position is used to compress the feedstock sufficiently to provide a preformed tablet which can then be transported out of the reservoir to another station for further compression. A third position effects formation of a tablet within the accumulation chamber. The dossiter is used in combination with a fixed die punch. The dossiter is moved to the fixed die punch so that the open end of the chamber is supported thereover. The movable die punch is movable towards the open end of the chamber so as to compress the feedstock held therein into a tablet between the movable die punch and the fixed die punch.

In its method aspect the present invention provides a method for forming a tablet from tableting feedstock. A feedstock dossiter is provided having an accumulation chamber with an open end and a movable die punch supported therein. A premeasured volume of tableting feedstock is collected within the accumulation chamber. The dossiter is positioned over a forming member and the die punch is moved within the accumulation chamber towards the open end to compress the tableting feedstock into a tablet between the movable die punch and the forming member.

In one embodiment a fixed die punch is provided as the forming member and the open end of the dossiter accumulation chamber is moved over the fixed die punch so as to form the tablet.

As more particularly described by way of a preferred embodiment herein, an assembly for the formation of a tablet from tableting feedstock is provided. The assembly includes a support table for movably supporting a tablet package and defines a tablet accommodating location. A feedstock reservoir is positioned adjacent the support table for containing tableting feedstock and defining an accumulation location. A fixed die punch is positioned adjacent the support table and defines a tablet forming location. A feedstock dossiter having an open ended feedstock accumulation chamber includes a movable die punch therein. The die punch is movable within the chamber for movement towards and away from the open end. A movable support member supports the dossiter for movement among the accumulation location, the tablet forming location and the tablet accommodating location. Movement of the movable die punch away from the accumulation chamber open end at the accumulation location effects accumulation of the feedstock therein. Movement of the movable die punch towards the open end at the tablet forming location effects compression of the accumulated feedstock into a tablet. Further movement of the movable die punch toward the open end at the tablet accommodation location effects ejection of the formed tablet into the tablet package.

BRIEF DESCRIPTION OF THE DRAWINGS

FIG. 5A shows the dossiter of FIG. 1 including accumulated tableting feedstock positioned over a fixed die punch.

FIG. 5B shows the compression of the tableting feedstock into a tablet over the fixed die punch with the dossiter of FIG. 5A.

FIG. 6 shows the step of ejecting the formed tablet from the dossiter into a product package.

FIG. 7 shows a form, fill and seal apparatus used to form tablets in accordance with the present invention.

FIGS. 8A–8C show successive operation of the dossiter employed in combination with the assembly of FIG. 7.

DETAILED DESCRIPTION OF THE PREFERRED EMBODIMENT

Figure 1:
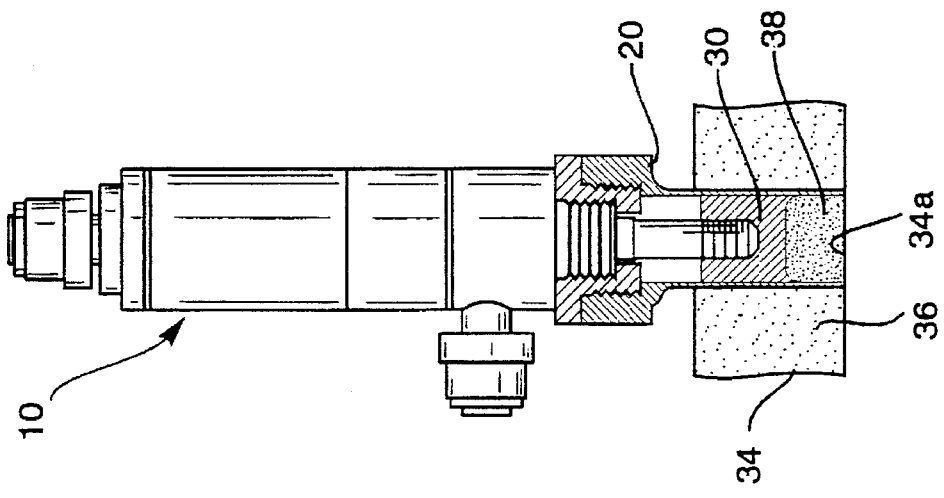
FIG. 1 is a front plan view of the tableting feedstock dossiter of the present invention.

The present invention is a unique method and apparatus for preparing compression dosage units, such as tablets, and for forming the units in the tablet package. The term "tablet" is used herein to mean a unit having two sides, sometimes referred to as a top and a bottom, and a continuous edge which joins the top and the bottom. The entire mass of the material throughout the tablet is the "volume" of the tablet.

The mass of the units prepared in accordance with the present invention is continuous in the sense that the feedstock material used to prepare the units (tableting feedstock) is prepared in a die or compression chamber "die cavity" and between the face of opposed compressors, sometimes referred to as "die punches", but which may have two different densities. A first volume is associated with the edge in that it circumscribes the unit and includes the edge surface. A second volume, which is referred to as the "non-edge" portion, is within the edge portion. In the present illustrative example the feedstock is collected, compressed and formed directly in a dossiter.

The method and apparatus of this invention are especially useful in making low density tablets and preferably tablets which undergo further curing or processing to form a rigid structure. The term low density is used herein to denote tablets wherein at least 60% and preferably 80% of the volume of the tablet has a density of less than 1.2 grams per cubic centimeter and preferably less than 0.8 grams per cubic centimeter. For preferred embodiments, the apparatus and process of the present invention are used to make high porosity tablets which have a porosity of 0.35 to 0.75 and preferably 0.45 to 0.65. Porosity as used herein is defines as: 1−(bulk density÷actual density).

The non-edge portion of units prepared in accordance with the invention has a lower density, mass per unit volume, than the edge portion. The non-edge volume density is less than about 1.2 grams per cubic centimeter, preferably less than 0.8 grams per cubic centimeter, and most preferably not greater than 0.6 grams per cubic centimeter.

The edge portion of tablets prepared according to the invention have a higher density than the non-edge portion. The edge portion has a density which is at least about 10% greater than the density of the non-edge portion, preferably about 15% greater, and most preferably about 20% greater. Thus, if the density of the non-edge portion is about 0.6 grams per cubic centimeter, the density of the edge portion is preferably about 0.66 grams per cubic centimeter, preferably about 0.69 grams per cubic centimeter, and most preferably about 0.72 grams per cubic centimeter.

The extent of the edge portion is that amount of volume and surface sufficient to increase the "strength" of the unit for handling by processing machinery and personnel without deterioration of the unit. "Strength" includes both resistance to unit fracture and surface crumbling, i.e., friability.

A tableting feedstock material which is particularly useful in the present invention is saccharide based. Particularly useful feedstocks for the tableting process of this invention are disclosed in U.S. application Ser. No. 08/259,496 (Attorney Docket No. 447-105) and U.S. application Ser. No. 08/259,258 (Attorney Docket No. No. 447-106).

In another embodiment, the feedstock disclosed in U.S. application Ser. No. 08/194,682 filed Feb. 10, 1994 (Attorney Docket No. 447-80), which includes a free form agglomerate wherein selected ingredients such as a medicinal substance, and a carrier are fused together, is used in the process of the present invention. The free form agglomerate is distinguished from agglomerates formed from wet and dry granulations. The components of the tablet are thoroughly dispersed throughout the product because the mixture attained in the free form agglomerate is microstructurally stabilized against migration out of mixture. Fusion of the ingredients in a micro-structurally-stabilized mixture is achieved prior to compression as a result of flash flow processing. The feedstock includes a saccharide-based material which acts as a carrier for the medicament.

Preferred materials useful as matrices may be chosen from such classes as sugars or sugar derivatives. The term sugar is meant to include those carbohydrates having a high glucose profile. A high glucose profile means that the carbohydrate has a large number of six-carbon mono and disaccharides as well as other glucose-based oligomers. Mono-, di-, tri- and polysaccharides and their derivatives may be employed. Examples include glucose, sucrose, maltose, lactose, arabinose, xylose, ribose, fructose, mannose, pentose, galactose sorbose, dextrose, sorbitol, xylitol, mannitol, pentatol, maltitol, isomalt, sucralose and mixtures thereof.

The carrier material can be selected from material which is capable of undergoing both physical and/or chemical changes associated with flash-flow processing. Materials useful as matrices may be chosen from those carbohydrates which are capable of forming free-form agglomerates upon being processed. Maltodextrins are an example of such carrier materials. Maltodextrins include those mixtures of carbohydrates resulting from hydrolysis of a saccharide feedstock which are described as solids having a DE of less than 45.

Polydextrose is also contemplated for use as a carrier. Polydextrose is a non-sucrose, essentially non-nutritive carbohydrate substitute. It can be prepared through polymerization of glucose in the presence of polycarboxylic acid catalyst and polyols. Generally, polydextrose is known to be commercially available in three forms: polydextrose A and polydextrose K, which are powdered solids, and polydextrose N supplied as a 70% solution. Each of these products also contain some low molecular weight components, such as glucose, sorbitol and certain oligomers. Regarding polydextrose, Applicants incorporate herein the contents of copending U.S. application Ser. No. 07/881,612 filed May 12, 1992 (Attorney Docket No. 447-46).

The feedstock can also include maltooligo-saccharide produced by selective hydrolysis of cornstarch followed by removal of high and low molecular weight compounds. The general description of malto-oligosaccharides as contemplated herein is set forth in above-identified U.S. application Ser. No. 07/847,595.

Referring now to the drawings, FIG. 1 shows a dossiter 10 of the present invention. Dossiter 10 is an elongate member including an upper portion 12 and an opposed lower portion 14. Upper portion 12 houses therein an operable mechanism (not shown) used to actuate dossiter 10 in accordance with the description set forth hereinbelow. Upper portion 12 may also include a connection device 16 which permits connection of an electrical or pneumatic control and power source to dossier 10. Lower portion 14 of dossiter 10 includes a mechanical coupling 18 which effects attachment of lower portion 14 to upper portion 12. In the present illustrative embodiment, screw threaded connection of lower portion 14 to upper portion 12 is contemplated.

Coupling 18 further supports as part of lower portion 14, an accumulation chamber 20, also referred to as a die 20. Accumulation chamber 20 is generally an elongate hollow cylindrical member having a closed first end 22 attached to coupling 18 and an opposed open end 24 defining a cylindrical die cavity 26 therebetween. Movably supported within die cavity 26 is an actuatable piston-like die punch 30 which is movable within die cavity 26 toward and away from open end 24. Die punch 30 is operable under the power mechanism connected to connection device 16 of dossiter 10 for controlled movement within die cavity 26 towards open end 24. Die punch 30 includes a tablet forming surface 32 facing open end 24 of chamber 20. The construction and shape of tablet forming surface 32 may be of the type more fully described in a commonly assigned U.S. patent application Ser. No. 08/438,165 bearing Attorney Docket No. 447-124 filed an even date herewith which is incorporated by reference herein.

As will be more fully described in further detail hereinbelow, dossiter 10 of the present invention may be used to collect a predetermined volume of tableting feedstock within die cavity 26 of accumulation chamber 20 and may be used to form a tablet within accumulation chamber 20 by movement of die punch 30.

Figure 2:
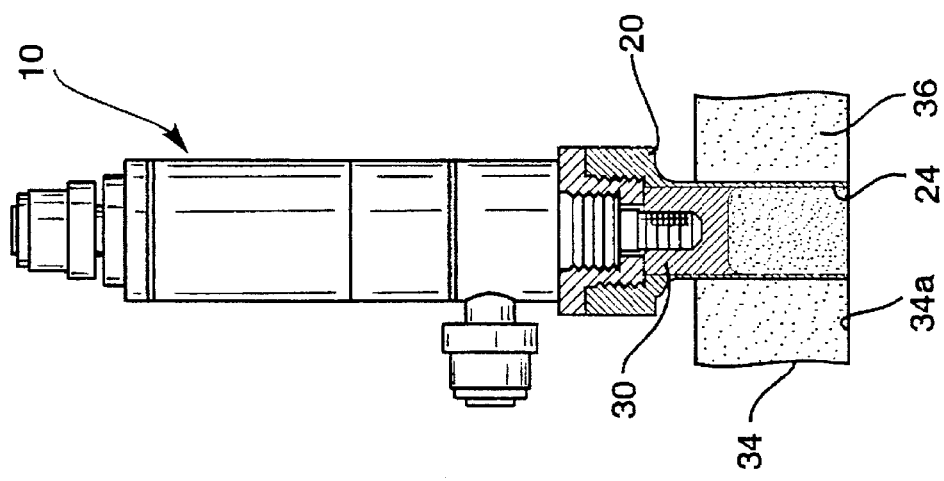
FIG. 2 shows the dossiter of FIG. 1 accumulating a volume of tableting feedstock from a reservoir.
Figure 3:
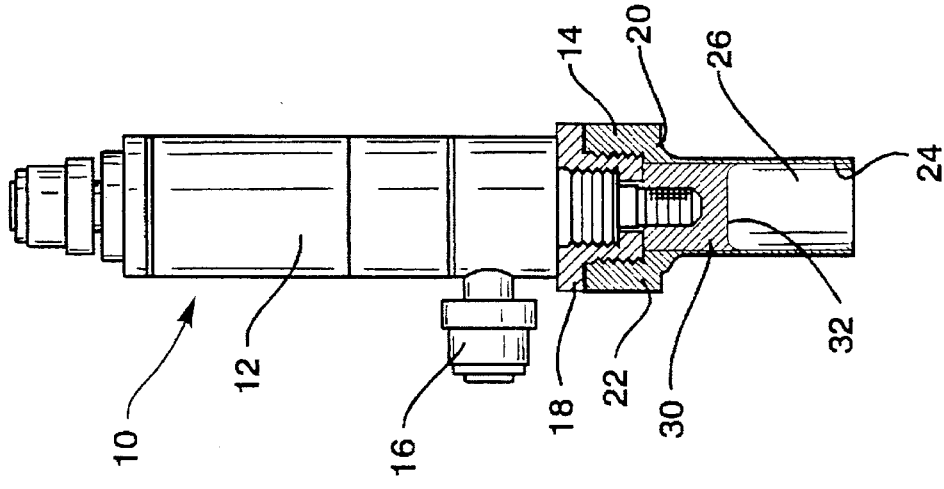
FIG. 3 shows the dossiter of FIG. 1 compressing the accumulated tableting feedstock into a tablet preform.

Referring now to FIGS. 2 and 3, dossiter 10 is shown with accumulation chamber 20 inserted into a reservoir 34 containing tableting feedstock 36. Reservoir 34 is of the type known in the art as a constant level reservoir having a bottom surface 34a against which the open end 24 of accumulation chamber 20 is placed. Constant level reservoir 34 is designed to provide a consistent level of tableting feedstock 36 at all times within the reservoir 34. In this manner a constant predetermined volume of tableting feedstock will be accommodated within die cavity 26 of accumulation chamber 20. When dossiter 10 is inserted into reservoir 34 the piston-like die punch 30 recedes upwardly towards closed end 22. As the die punch 30 retracts, feedstock 36 enters accumulation chamber 20 until the open end 24 is seated against the bottom surface 34a. Once the dossiter 10 is fully inserted into reservoir 34 and a predetermined volume of tableting feedstock is accumulated within die cavity 26 of accumulation chamber 20, dossiter 10 may be moved to a position adjacent a fixed tablet forming member (such as a fixed die punch) which is used in combination with movable die punch 30 to form a tablet from the tableting feedstock directly within the die cavity 26 of accumulation chamber 20.

Prior to such movement, as shown in FIG. 3, the predetermined volume of tableting feedstock held within die cavity 26 may optionally be compressed into a tablet preform by partial movement of die punch 30 in a direction towards open end 24 of accumulation chamber 20. The predetermined volume of tableting feedstock supported therein is thereby slightly compressed into a low density tablet preform 38 against the bottom surface 34a of reservoir 34. The density of tablet preform 38 may be controlled by controlling the distance that die punch 30 moves within accumulation chamber 20. By compressing the tableting feedstock 36 into low density tablet preform 38, movement of the mass of tableting feedstock 36 by dossiter 10 is more easily facilitated. Surface friction between the inner wall of die cavity 26 and the slightly compressed preform, retains the preform 38 within cavity 26. However, even absent the formation of tablet preform 38, the tableting feedstock 36 contained within die cavity 34 may be moved, upon the movement of dossiter 10 without loss of the contents as the insertion of the open ended accumulation chamber into the filled reservoir establishes a vacuum holding the contents therein.

Figure 4A:
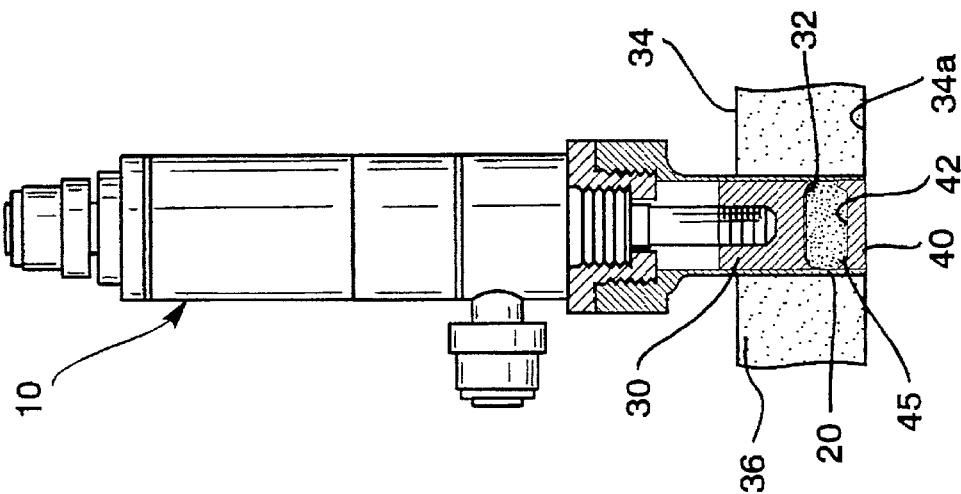
FIG. 4A shows the dossiter of FIG. 1 positioned over a fixed die punch supported within the tableting reservoir.
Figure 4B:
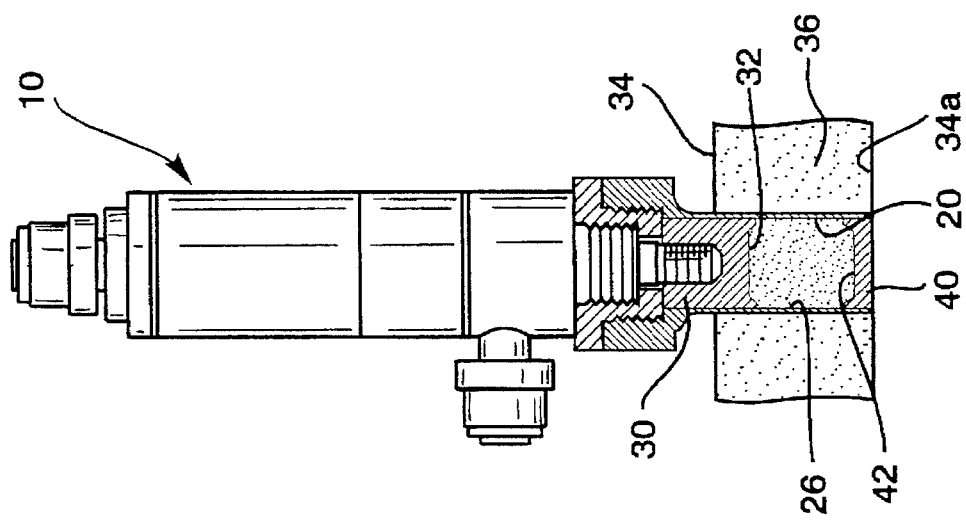
FIG. 4B shows the compression of the feedstock into a tablet with the dossiter shown in FIG. 4A.

Referring to FIGS. 4A and 4B, the formation of a tablet within the die cavity 26 of accumulation chamber 20 is shown. In one embodiment of the present invention, one or more fixed die punches 40 may be supported on the bottom surface 34a of reservoir 34. The dossiter is inserted into the reservoir, filling the dossiter with feedstock and is further positioned over fixed die punch 40 in reservoir 34. Fixed die punch 40 may have a tablet forming Surface 42 of similar configuration to tablet forming surface 32 of movable die punch 30. The respective tablet forming surfaces are positioned in facing opposition so as to form a tablet 45 therebetween. Operable movement of movable die punch 30 within accumulation chamber 20 by the mechanism of dossiter 10 moves die punch 30 towards fixed die punch 40 so as to compress the tableting feedstock 36 (or the preform 38) between the opposed tablet forming surfaces 32 and 42 of movable die punch 30 and fixed die punch 40 respectively. The density of the tablet 45 formed between the die punches 30 and 40 is controlled by controlling the distance that the movable die punch 30 is moved within accumulation chamber 20. Alternatively, density of the formed tablet 45 may be controlled by controlling the force applied by the movable die punch 30. Thus, as shown in FIGS. 4A and 4B, a tablet 45 may be formed directly within the accumulation chamber of dossiter 10 between the movable die punch 30 supported therein and a fixed die punch 40 supported within the tableting feedstock reservoir.

A further embodiment of the present invention is shown in FIGS. 5A and 5B where tablet 45 is formed within the die cavity 26 of accumulation chamber 20 over a fixed die punch 50 supported externally of the tableting feedstock reservoir 34. One or more fixed die punches 50 may be supported on a die punch platform 53 at a location externally spaced from reservoir 34. Again, fixed die punch 50 is of construction similar to the previously described die punches having a tablet forming surface 52. Dossiter 10 is removed from reservoir 34 (FIGS. 2 or 3) and with die cavity 26 supporting either tableting feedstock 36 or tableting feedstock formed into tablet preform 38, is positioned over fixed die punch 50. The open end 24 of accumulation chamber 20 is inserted over fixed die punch 50 so as to accommodate tableting feedstock 36 (or preform 38) between the opposed tablet forming surfaces 32 and 52. As shown in FIG. 5B in a manner similar to that described with respect to FIG. 4B, movable die punch 30 may be moved towards the open end 24 of accumulation chamber 20 to compress tableting feedstock 36 into tablet 45 against fixed die punch 50. In the above described embodiments movable die punch 30 is moved towards fixed die punch 50. It is within the contemplation of the present invention to provide die punch 50, to be movably positioned so as to travel into accumulation chamber 20 of dossiter 10. Such movement can be partially or totally into accumulation chamber 20 to compress the feedstock therein.

With respect to the embodiment shown in FIGS. 4A and 4B and 5A and 5B, the dossiter 10 of the present invention provides for the formation of tablet 45 directly within the accumulation chamber used to accumulate the tableting feedstock. After formation, the tablet may be transferred within the dossiter 10 to a location where further processing takes place. The tablet 45 may be retained in accumulation chamber 20 during transference in a manner more fully described in above incorporated commonly assigned patent application Ser. No. 08/438,165 bearing Attorney Docket No. 447-124. As shown in FIG. 6, the formed tablet 45 is transferred to a product package 60 where further movement of movable die punch 30 towards open end 24 of accumulation chamber 20 causes ejection of the tablet 45. The tablet 45 is ejected into a cavity 62 of package 60. The package 60 may now undergo further processing for ultimate distribution.

The present invention contemplates, in a further embodiment, the use of dossiter 10 to form a tablet with accumulation chamber 20 directly within a tablet package so as to eliminate the need to transfer the formed tablet to the package itself. The ability to form a tablet directly in the tablet package is more fully described in commonly assigned copending U.S. patent application Ser. No. 08/438, 239 bearing Attorney Docket No. 447-123 filed an even date herewith and incorporated by reference herein.

Concepts of the present invention may be practiced in an automated tableting apparatus shown more specifically in FIG. 7. Tableting apparatus 70 is a form, fill and seal machine designed for in-line operation in a full production. Tableting apparatus 70 forms a tablet package from plastic sheeting, compresses tablets from tableting feedstock, fills the package with formed tablets and seals the package in a single continuous operation. Tableting apparatus 70 is a computer controlled automated assembly apparatus which includes an elongate lower cabinet 72 housing an upper longitudinal table 74 extending between opposite ends 74a and 74b. Table 74 is movable in a linear fashion under the operation of an electromechanical drive mechanism (not shown) operated by one or more controllers. A roll of blister or cavity forming sheeting 76 such as a plastic sheeting or aluminum/plastic foil laminate is fed into cabinet 72 where cavities are formed in the planar sheeting. The cabinet 72 may contain a heating element and forming dies, preferably a vacuum forming die (not shown) for the formation of continuously joined product trays 60. Product packages or trays 60 of the type described above are successively positioned on table 74 for movement therealong. While not specifically shown herein, table 74 may include provisions for a package support platform for the fixed accommodation of tablet packages 60 thereon.

Tableting apparatus 70 defines a first location 75 providing for the accumulation of tableting feedstock. First location 75 includes constant level feedstock reservoir 34 containing tableting feedstock 36. Tableting apparatus 70 defines a second location 77 for the formation of tablets 45 (FIG. 4). Second location 77 includes an array of fixed die punches 50. The array of fixed die punches 50 may be appropriately supported on a platform 78. Table 74 supporting packages 60 defines a third location 79 where formed tablets 45 may be ejected into the cavities 62 of the packages for further processing.

Supported among the first, second and third locations is a dossiter support turret assembly 80. In the present illustrative embodiment dossiter support turret assembly 80 includes a drum-like turret head 82 which is rotatably movable in a clockwise direction. Turret head 82 supports, adjacent the lower end thereof, three circumferentially spaced depending arms 84. Each arm supports at the end thereof an array 86 of dossiters 10. Array 86 may include individual dossiters 10 of the type shown and described above, arranged in a pattern matching the pattern of fixed die punches 50 at second location 77. One feature of the array of dossiters 10 is that each dossiter can apply uniform pressure to each tablet upon formation. As each dossiter 10 is individually controlled the feedstock (or preform) is compressed individually to a preselected density. In the present illustrative example an array of thirty-six dossiters is provided. This is also designed to match the pattern of cavities 62 in a particular tablet package 60. Each array 86 of dossiters 10 is constructed to be identical and to be rotatably movable in an indexed fashion upon rotative movement of turret head 82. Each array 86 is movable among the first, second and third locations in sequential fashion so as to collect tableting feedstock 36 within the dossiter, form a tablet with fixed dies 50 and eject the formed tablets into tablet package 60.

With references to FIGS. 7 and 8A–8C, one sequence may be described. One array 86 of dossiters 10 is initially positioned over reservoir 75. Each array 86 is supported on arm 84 in a manner which permits vertical movement thereof in the direction of arrow A. Downward movement of array 86 into reservoir 76 effects accumulation of a preselected amount of tableting feedstock within the accumulation chambers of each of the dossiters in a manner described hereinabove. At this first accumulation location, tableting feedstock 36 is accumulated within the accumulation chamber 20 by lowering the dossiter into the reservoir 75 wherein the die 30 is moved upward as the feedstock fills the dossiter. The array 86 is then raised from reservoir 76. Turret head 82 (FIG. 7) is rotated in a clockwise direction to bring the one array 86 to second location 77 above die platform 78. The one array 86 is then lowered over the array of fixed dies 50 so that the open ends 24 of each accumulation chamber 20 is positioned over an individual fixed die 50 as described above. As shown in FIG. 8B, movable die punch 30 is moved towards the open end 24 of accumulation chamber 20 to compress the tableting feedstock between movable die punch 30 and fixed die punch 50 into tablet 45. The one array 86 is again raised off of fixed dies 50 with the formed tablets 45 being retained within accumulation chamber 20 of the dossiters 10. It is contemplated that the formed tablets 45 may be retained within accumulation chamber 20 upon the removal from fixed dies 50 by formation of the tablet 45 in a manner more fully described in above-incorporated copending U.S. patent application Ser. No. 08/438,165 bearing Attorney Docket No. 447-124. Turret head 82 is again moved in a clockwise fashion to bring the one array 86 to third location 79 over table 74. In this position the array 86 may be again lowered to place each accumulation chamber 20 adjacent a cavity 62 of product package 60. Further downward movement of movable die punch 30 as shown in FIG. 8C effects ejection of the tablets 45 from the accumulation chambers 20 into the cavities 62 of package 60 in a manner described above. As may be readily appreciated, array 86 may be again moved from the third location 79 back to first location 75 to effect sequential continuous operation of the tableting apparatus 70 as the next sequential product package 60 is indexed along table 74.

The filled product packages 60 are sequentially indexed along table 74, whereupon the next successive package 60 is filled.

The filled product package 60 is then linearly moved from third station 79 to a subsequent station 90, where various additional processing steps may be accomplished. For example, inspection of the product trays may take place. Such inspection would include assuring that each cavity is filled with a tablet and that the tablets are of correct size and weight.

After inspection has taken place the product packages may be moved along table 74 to one or more additional stations 92 where further secondary operations may take place. Such secondary operations may include curing the tablets by heat, steam, moisture or other means, placing a sealing lid over the product package, die cutting the package and the sealing lid, as well as labeling the tablet or package (such as by ink jet printing, pad printing, gravure printing or other printing techniques) and boxing the package.

Thus, while there have been described what are presently believed to be preferred embodiments of the present invention, those skilled in the art would realize that other and further modifications and changes can be made without the parties in the true spirit of the invention and is intended to include all such further changes and modifications as come within the scope of this invention.

What is claimed is:

1. An apparatus useful in the formation of a dosage tablet from tableting feedstock held in a reservoir comprising:
   a feedstock dossiter having an open ended chamber for insertion into said tableting feedstock reservoir; and
   a movable die punch movable within said chamber between at least two positions, a first position effecting collection of a preselected volume of tableting feedstock and a second position effecting formation of said tablet within said chamber.

2. An apparatus of claim 1 wherein said movable die punch is operably movable within said chamber.

3. An apparatus of claim 2 wherein said movable die punch is movable away from said open end of said chamber in said first position.

4. An apparatus of claim 3 further including means engageable with said dossiter for forming said tablet with said movable die punch.

5. An apparatus of claim 4 wherein said dossiter engagement means includes a fixed die punch insertable into said open end of said chamber to form said tablet between said movable die punch and said fixed die punch upon movement of said movable die punch to said second position.

6. An apparatus of claim 5 wherein said fixed die punch is located at a fixed position outside of said feedstock reservoir.

7. An apparatus of claim 5 wherein said fixed die punch is located within said feedstock reservoir.

8. An apparatus of claim 3 wherein said movable die punch is movable from said first position to an intermediate position within said reservoir to compress said feedstock accumulated in said chamber into a tablet preform.

9. A method of forming a low density tablet from tableting feedstock comprising the steps of:
   providing a feedstock dossiter having an accumulation chamber including an open end and a movable die punch movably supported therein;
   collecting a premeasured volume of said tableting feedstock in said accumulation chamber;
   positioning said open end of said dossiter accumulation chamber over a forming member; and
   moving said movable die punch towards said open end of said accumulation chamber to compress said tableting feedstock into a tablet between said movable die punch and said forming member.

10. A method of claim 9 further including the step of providing a reservoir containing said tableting feedstock.

11. A method of claim 10 wherein said collecting step further includes inserting said dossiter accumulation chamber into said feedstock reservoir.

12. A method of claim 11 wherein said movable die punch is movable toward and away from said open end of said dossiter accumulation chamber.

13. A method of claim 12 wherein said collecting step further includes moving said movable die punch away from said open end of said dossiter accumulation chamber.

14. A method of claim 13 further including the step of moving said die punch within said dossiter accumulation chamber to an intermediate position spaced from the open end thereof to compress said feedstock collected therein into a tablet preform.

15. A method of claim 13 further including the step of providing said forming member as a fixed die punch.

16. A method of claim 15 wherein said positioning step further includes inserting said open end of said accumulation chamber over said fixed die punch.

17. A method of claim 16 wherein said forming member providing step further includes providing said fixed die punch within said feedstock reservoir.

18. A method of claim 16 wherein said forming member providing step further includes providing said fixed die punch at a location exterior of said feedstock reservoir.

19. An assembly for the formation of a tablet from tableting feedstock comprising:
   a support table for movably supporting a tablet package and defining a tablet accommodating location;

a feedstock reservoir positioned adjacent said support table for containing said tableting feedstock and defining an accumulation location;

a fixed die punch positioned adjacent said support table and defining a tablet forming location;

a feedstock dossiter, said dossiter having an open ended feedstock accumulation chamber and a movable die punch movably supported within said accumulation chamber for movement toward and away from said open end; and movable support means for supporting said dossiter for movement among said accumulation location, said tablet forming location and said tablet accommodating location;

movement of said movable die punch away from said accumulation chamber open end at said accumulation location effecting accumulation of said feedstock therein;

movement of said movable die punch toward said open end of said accumulation chamber at said tablet forming location effecting compression of said accumulated feedstock into said tablet; and further movement of said movable die punch toward said open end of said accumulation chamber at said tablet accumulating location effecting ejection of said formed tablet into said tablet package.

20. An assembly of claim 19 wherein said movable support means includes a rotatable support element positioned adjacent said support table, said dossiter being affixed to said rotatable support element for rotatable movement therewith.

21. An assembly of claim 20 wherein said movable support means supports at least three said dossiters in spaced positioned thereon, one of said at least three dossiters being positioned at each of said tablet accommodating position, said accumulation location and said tablet forming location, each of said dossiters being sequentially indexed among said locations.

22. An assembly of claim 19 wherein said fixed die punch is positioned within said feedstock reservoir.

23. An assembly of claim 19 wherein said fixed die punch is located at a position exteriorly spaced from said feedstock reservoir.

24. An assembly of claim 19 further including a dossiter array, said array including a plurality of said dossiters.

25. An assembly of claim 24 further including a fixed die punch array, said array including a plurality of fixed die punches arranged in a pattern corresponding to the pattern of said dossiter array.

26. An assembly of claim 25 wherein said support table supports said tablet package having a plurality of said tablet cavities therein, said cavities being arranged in a pattern corresponding to the pattern of said dossiter array and said fixed die punch array.

* * * * *